US009062206B2

(12) United States Patent
Gharda

(10) Patent No.: US 9,062,206 B2
(45) Date of Patent: *Jun. 23, 2015

(54) BIS-QUINOPHTHALONE PIGMENT AND A PROCESS FOR PREPARING THE SAME

(71) Applicant: Keki Hormusji Gharda, Maharashtra (IN)

(72) Inventor: Keki Hormusji Gharda, Maharashtra (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/353,442

(22) PCT Filed: Oct. 22, 2012

(86) PCT No.: PCT/IN2012/000695
§ 371 (c)(1),
(2) Date: Apr. 22, 2014

(87) PCT Pub. No.: WO2013/098836
PCT Pub. Date: Jul. 4, 2013

(65) Prior Publication Data
US 2014/0288311 A1   Sep. 25, 2014

(30) Foreign Application Priority Data

Oct. 24, 2011   (IN) .......................... 2991/MUM/2011

(51) Int. Cl.
*C07D 215/40*   (2006.01)
*C09B 25/00*   (2006.01)

(52) U.S. Cl.
CPC .............. *C09B 25/00* (2013.01); *C07D 215/40* (2013.01)

(58) Field of Classification Search
CPC ..... C07D 215/40; C09B 25/00; A01B 12/006
USPC ......................................................... 546/171
See application file for complete search history.

(56) References Cited

U.S. PATENT DOCUMENTS

| 5,106,980 A | 4/1992 | Ort et al. | |
| 2014/0296529 A1* | 10/2014 | Gharda | ........................ 546/171 |

FOREIGN PATENT DOCUMENTS

| DE | 429176 | 5/1926 |
| DE | 2530123 A1 | 1/1977 |
| EP | 0463477 A1 | 1/1992 |

OTHER PUBLICATIONS

Miyatake Masayoshi, Ehashi Shigeyuki, Study on Quinophthalone Pigments, Shikizai Kyokaishi, 1971,p. 316-324, vol. 44, Japan.

* cited by examiner

*Primary Examiner* — D M Seaman
(74) *Attorney, Agent, or Firm* — Muncy, Geissler, Olds & Lowe, P.C.

(57) ABSTRACT

The present disclosure relates to a bis-quinophthalone pigment of Formula I, and a process for the same.

wherein $X_1$, $X_2$, $X_3$ and $X_4$ are independently H or halogen, preferably Cl or Br; $R_2$ is substituent selected from the group consisting of H, $C_1$-$C_{20}$ straight or branched chain alkyl substituents, aromatic substituents, aliphatic substituents, and combinations thereof.

14 Claims, No Drawings

BIS-QUINOPHTHALONE PIGMENT AND A PROCESS FOR PREPARING THE SAME

CROSS REFERENCE TO RELATED APPLICATIONS

This application is a national stage of International Application No.: PCT/IN2012/000695, which was filed on Oct. 22, 2012, and which claims priority to 2991/MUM/2011 which was filed on Oct. 24, 2011, and which are both herein incorporated by reference.

FIELD OF THE DISCLOSURE

The present disclosure relates to quinophthalone pigments. The present disclosure particularly relates to bis-quinophthalone pigments and a process for preparing the same.

BACKGROUND

Pigments are known to have wide applications in human life such as coatings, paints, papers, adhesives, latexes, toners, textiles, fibers, plastics, cosmetics and inks. When the white light of 380 or 400 nanometers to 760 or 780 nanometers encounters a pigment, a part of spectrum is absorbed by the conjugated chemical bonds and other components present in the pigment. Other non-absorbed part is reflected or scattered. The reflected or scattered wavelength imparts color to the pigment. This knowledge of absorption and reflection by a particular chemical compound is being used to develop the variety of pigments.

A large number of organic and inorganic yellow pigments are available. They differ by their brightness of shade, opacity, fastness requirements, physiological properties, and economic considerations. These properties influence the choice of the pigments depending on the end application. As well as being used in yellow paints, yellow pigments are also used in oranges, greens and browns. Quinophthalone pigment is an organic yellow pigment used as a chrome replacement in high quality finishes. Quinophthalone pigment is prepared from quinaldine compounds.

Co-pending application 2990/MUM/2011 discloses new bis-quinaldine compounds.

German Patent 429176 discloses a process of preparing mono quinophthalones by reacting 3-hydroxy quinaldine with anhydride or imide of dicarboxylic acid followed by either halogenation or sulphonation reaction at 3-hydroxy position.

U.S. Pat. No. 5,106,980 discloses a process of preparing mono quinophthalones by condensing 8-aminoquinaldine with an optionally substituted phthalic anhydride in presence of molten benzoic acid as diluent at a temperature ranging between 123° C. to 200° C.

A method for preparation of bis quinophthalones having hydrogen or chlorine or methyl substituent at 8-position is disclosed in an article titled "Study on Quinophthalone Pigments", Shikizai Kyokaishi, 44 (1971), 316-324. The method includes reacting fused phthalic anhydride with 6,6'-bis quinaldine and heating at 170° C. to 180° C. for 6 hours to 12 hours.

However, Bis-quinophthalones disclosed in Shikizai Kyokaishi, 44 (1971), 316-324, shows remarkable color fading when exposed for longer hours and are poor light resistant.

The mono-quinophthalone and bis-quinophthalone of the prior art typically, suffer from drawbacks such as poor light resistance, poor solvent resistance, poor hue and less stability.

Thus, there is felt a need to develop new bis-quinophthalone pigments which can obviate the drawbacks associated with the prior art.

OBJECTS OF THE DISCLOSURE

It is an object of the present disclosure to provide a bis-quinophthalone pigment which is light resistance and solvent resistance.

It is another object of the present invention to provide a bis-quinophthalone pigment which is stable.

It is yet another object of the present disclosure to provide a feasible process for the preparation of bis-quinophthalone pigment.

SUMMARY

In accordance with the present disclosure there is provided a bis-quinophthalone pigment of Formula (I)

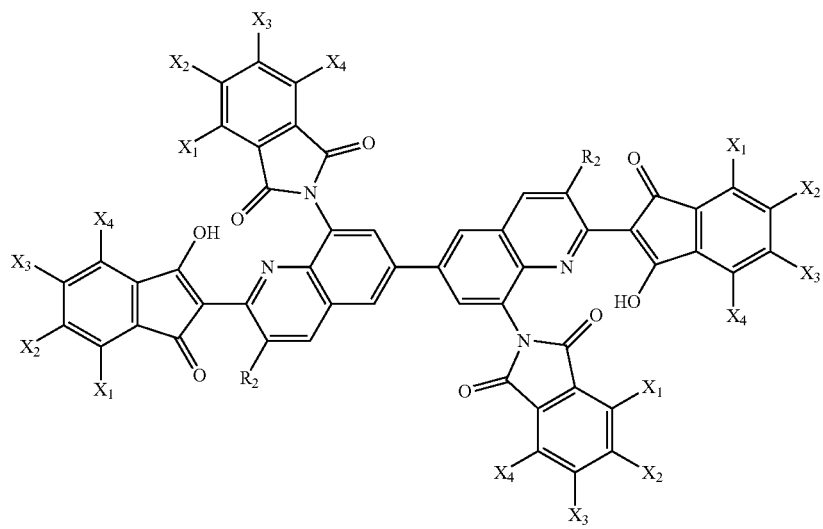

Formula (I)

wherein $X_1$, $X_2$, $X_3$ and $X_4$ are independently H or halogen, preferably Cl or Br;

$R_2$ is substituent selected from the group consisting of H, $C_1$-$C_{20}$ straight or branched chain alkyl substituents, aromatic substituents, aliphatic substituents, and combinations thereof.

Preferably, the substituent include but is not limited to amines, substituted amines, aromatic amines, aliphatic alcohols, aromatic alcohols, aliphatic carboxylic acids, aromatic carboxylic acids, phenols, aliphatic or aromatic ethers and the like.

In a preferred embodiment of the present disclosure, $R_2$ is H and $X_1$, $X_2$, $X_3$ and $X_4$ is Cl.

In another aspect of the present disclosure there is provided a process for preparing a compound of Formula (I); said process comprising the following steps:

i. Condensing a Compound of Formula (II)

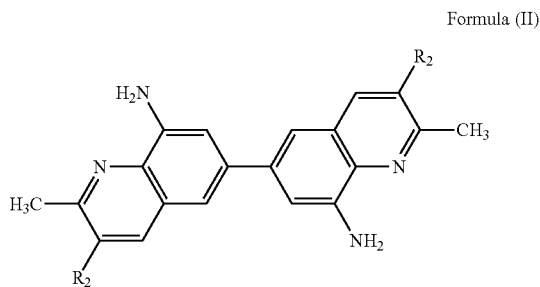

Formula (II)

Wherein $R_2$ is a substituent selected from the group consisting of H, $C_1$-$C_{20}$ straight or branched chain alkyl substituents, aromatic substituents, aliphatic substituents and combinations thereof.

with substituted phthalic anhydride of Formula (III)

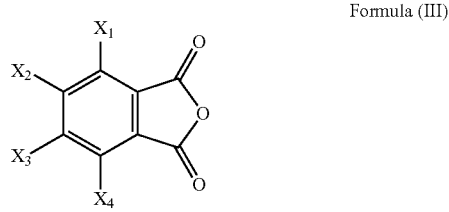

Formula (III)

wherein $X_1$, $X_2$, $X_3$ and $X_4$ are independently H or halogen, preferably Cl or Br, to obtain crude bis-quinophthalone compound of Formula (I); and ii. Pigmenting Crude bis-quinophthalone Compound to Obtain a bis-quinophthalone Pigment of Formula (I).

Typically, the process step of condensing is carried out in the presence of monochlorobenzene and benzoic acid at a temperature in the range of 90° C. to 250° C.

Typically, the amount of monochlorobenzene is in the range of 1500 ml to 3000 ml per mole of compound of Formula (II).

Typically, the compound of Formula (II) is 8,8'-diamino-6,6'-bis quinaldine.

Typically, the amount of benzoic acid is in the range of 3000 gm to 6000 gm per mole of compound of Formula (II).

Typically, the amount of phthalic anhydride of formula (III) is in the range of 4.0 moles to 6.0 moles per mole of compound of Formula (II).

Typically, the compound of formula III is tetrachloro phthalic anhydride.

Typically, the step of pigmenting is carried in presence of at least one polar solvent selected from the group consisting of dimethyl acetamide, dimethyl formamide, N-methylpyrrolidone and isobutyl alcohol, at a temperature in the range of 80° C. to 150° C.

Typically, the crude pigment is ball milled for a period of about 20 hours to 36 hours before pigmenting with polar solvent.

In another embodiment of the present disclosure, the crude pigment is ball milled with a salt for a period of about 20 hours to 36 hours before pigmenting with polar solvent Typically, the salt is at least one selected from the group consisting inorganic salts and organic salts, preferably sodium sulphate.

Typically, the amount of dimethyl acetamide is in the range of 8 ml to 16 ml per gm of crude pigment.

DETAILED DESCRIPTION OF THE DISCLOSURE

The present disclosure provides a bis-quinophthalone pigment of Formula (I)

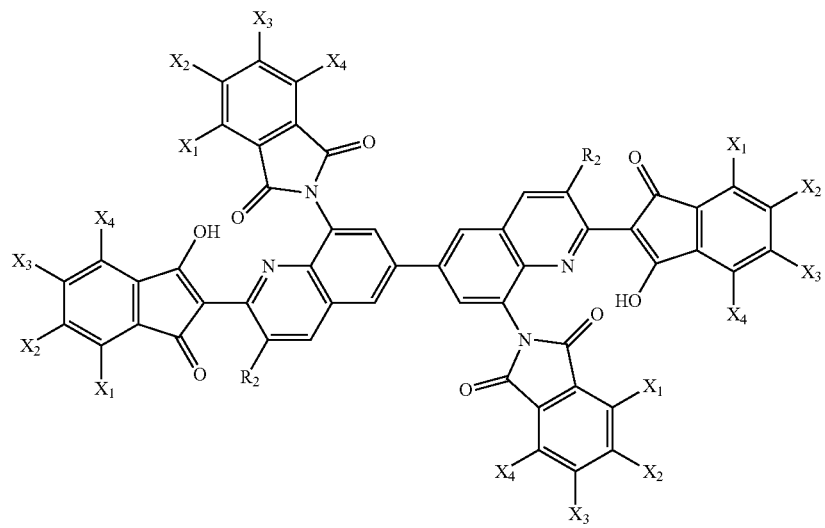

I wherein $X_1, X_2, X_3$ and $X_4$ are independently H or halogen, preferably Cl or Br;

$R_2$ is substituent selected from the group consisting of H, $C_1$-$C_{20}$ straight or branched chain alkyl substituents, aromatic substituents, aliphatic substituents, and combinations thereof.

Preferably, the substituent include but is not limited to amines, substituted amines, aromatic amines, aliphatic alcohols, aromatic alcohols, aliphatic carboxylic acids, aromatic carboxylic acids, phenols, aliphatic or aromatic ethers and the like.

Quinophthalone pigments are generally prepared from quinaldine compounds.

The present disclosure provides a process for preparing the bis-quinophthalone pigment of formula I using the bis-quinaldine compound of formula II.

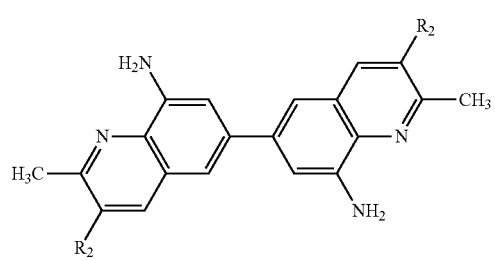

II

Wherein $R_2$ is a substituent selected from the group consisting of H, $C_1$-$C_{20}$ straight or branched chain alkyl substituents, aromatic substituents, aliphatic substituents and combinations thereof.

The process step in accordance with the present disclosure involves a condensation of a compound of formula II with substituted phthalic anhydride of Formula (III)

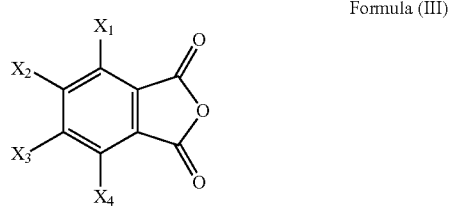

Formula (III)

wherein $X_1, X_2, X_3$ and $X_4$ are independently H or halogen, preferably Cl or Br, in presence of monochlorobenzene and benzoic acid at a temperature in the range of 90° C. to 250° C., to obtain crude bis-quinophthalone compound of Formula (I) and pigmenting the crude bis-quinophthalone compound to obtain a bis-quinophthalone pigment of formula (I).

The amount of monochlorobenzene is in the range of 1500 ml to 3000 ml per mole of compound of Formula (II).

The amount of benzoic acid is in the range of 3000 gm to 6000 gm per mole of compound of Formula (II).

The amount of phthalic anhydride of formula (III) is in the range of 4.0 moles to 6.0 moles per mole of compound of Formula (II).

The step of pigmentation of crude bis-quinophthalone compound is carried out in the presence of polar solvent. The polar solvent includes dimethyl acetamide, dimethyl formamide, N-methylpyrrolidone and isobutyl alcohol. Most preferred solvent is dimethyl acetamide. The amount of dimethyl acetamide is in the range of 8 ml to 16 ml per gm of crude pigment.

The pigmentation is carried out at a temperature ranging between 80° C. to 150° C.

The crude pigment is ball milled for a period of about 20 hours to 36 hours before pigmenting with polar solvent.

In another embodiment of the present disclosure, the crude pigment is ball milled with a salt for a period of about 20 hours to 36 hours before pigmenting with polar solvent. The salt is at least one selected from the group consisting inorganic salts and organic salts. The salt is preferably sodium sulphate.

In preferred embodiment of the present disclosure, the compound of Formula (II) is 8,8'-diamino-6,6'-bis quinaldine.

The present disclosure is further illustrated with the help of the following examples which should not be construed as limiting.

EXAMPLES

Step-1: Preparation of Crude Pigment-G

Example 1

Preparation of Crude Pigment G
(Bis-Quinophthalone Pigment Crude)

635 gm of benzoic acid and 151 gm of tetrachloro phthalic anhydride were added slowly to 320 ml of monochlorobenzene solvent at 90° C. The temperature was then raised to 160° C. in 2 hours to obtain a mixture. To this mixture was added a hot solution of monochlorobenzene containing 40 gm of Bis-8-aminoquinaldine (0.126 moles), over a period of 3.5 hours. The resulting reaction mixture was heated to 180 to 200° C. for a period of 3.5 hours and further maintained for 3.5 hours. The temperature of the reaction mixture was raised to 205° C. and maintained with stirring for another two hours. Before cooling to 150° C., 1270 ml of monochlorobenzene was slowly added to the reaction mixture. The mixture was filtered at 125° C. The obtained solid mass was washed with hot monochlorobenzene and water. The product was dried to yield crude 150 gm, (85%) of bis-quinophthalone pigment (crude pigment G).

Example-2

Preparation of Crude Pigment G
(Bis-Quinophthalone Pigment Crude)

508 gm of benzoic acid and 151 gm of tetrachloro phthalic anhydride were added slowly to 320 ml of monochlorobenzene solvent at 90° C. The temperature was then raised to 160° C. in 2 hours to obtain a mixture. To this mixture was added a hot solution of monochlorobenzene containing 40 gm of Bis-8-aminoquinaldine, over a period of 3.5 hours. The resulting reaction mixture was heated to 180 to 200° C. for a period of 3.5 hours and further maintained for 3.5 hours. The temperature of the reaction mixture was raised to 205° C. and maintained with stirring for another two hours. Before cooling to 150° C., 1270 ml of monochlorobenzene was slowly added to the reaction mixture. The mixture was filtered at 125° C. The obtained solid mass was washed with hot monochlorobenzene and water. The product was dried to yield crude 141 gm (80%) bis-quinophthalone pigment (crude pigment G).

Example-3

635 gm of benzoic acid and 151 gm of tetrachloro phthalic anhydride were added slowly to 320 ml of monochlorobenzene solvent at 90° C. The temperature was then raised to 160° C. in 2 hours to obtain a mixture. To this mixture was added a hot solution of monochlorobenzene containing 40 gm of Bis-8-aminoquinaldine, over a period of 3.5 hours. The resulting reaction mixture was heated to 180° C. for a period of 3.5 hours and further maintained for 6 hours. Before cooling to 150° C., 1270 ml of monochlorobenzene was slowly added to the reaction mixture. The mixture was filtered at 125° C. The obtained solid mass was washed with hot monochlorobenzene and water. Finally, the product was dried to yield 123.2 gm (70%) crude bis-quinophthalone pigment (crude pigment G).

Example-4

635 gm of benzoic acid and 182 gm of tetra chloro phthalic anhydride were added slowly to 320 ml of monochlorobenzene solvent at 90° C. The temperature was then raised to 160° C. in 2 hours to obtain a mixture. To this mixture was added a hot solution of monochlorobenzene containing 40 gm of Bis-8-aminoquinaldine, over a period of 3.5 hours. The resulting reaction mixture was heated to 180 to 200° C. for a period of 3.5 hours and further maintained for 3.5 hours. The temperature of the reaction mixture was raised to 205° C. and maintained with stirring for another two hours. Before cooling to 150° C., 1270 ml of monochlorobenzene was slowly added to the reaction mixture. The mixture was filtered at 125° C. The obtained solid mass was washed with hot monochlorobenzene and water. Finally, the product was dried to yield 152 gm (86%) crude bis-quinophthalone pigment (crude pigment G).

Step-2: Pigmentation

Example-5

A mixture of 100 gm of crude Pigment G [ball milled with sodium sulphate (85 part pigment: 15 part sodium sulphate) for 24 hours] and 1200 ml dimethyl acetamide was heated to 127° C. and maintained at 127° C. for 2 hours. The mixture was then cooled to 100° C., filtered and washed with dimethyl acetamide and water. The obtained product was dried to obtain dry pigment G (90 gm, 90%). The pigment shows good light fastness.

Example-6

A mixture of 100 gm of crude Pigment G [ball milled with salt sodium sulphate (85 part pigment: 15 part sodium sulphate) for 24 hours] and 1200 ml N-methylpyrrolidone was heated to 127° C. and maintained at 127° C. for 2 hours. The mixture was then cooled to 100° C., filtered and washed with N-methylpyrrolidone and water. The obtained product was dried to obtain dry pigment G (89 gm, 89%). The pigment is more solvent resistant.

Example-7

A mixture of 100 gm of crude Pigment G [ball milled with salt sodium sulphate (85 part pigment: 15 part sodium sulphate) for 35 hours] and 1200 ml dimethyl acetamide was heated to 127° C. and maintained at 127° C. for 2 hours. The mixture was then cooled to 100° C., filtered and washed with dimethyl acetamide and water. The obtained product was dried to obtain dry pigment G (90 gm, 90%). The pigment has good light fastness. The tinting shade is 10% stronger than example-5.

Example-8

A mixture of 100 gm of crude Pigment G [ball milled with Sodium sulphate in the ratio 70 part pigment: 30 part sodium sulphate for 24 hours] and 1200 ml dimethyl acetamide was heated to 127° C. and maintained at 127° C. for 2 hours. The mixture was then cooled to 100° C. filtered and washed with dimethyl acetamide and water. The obtained product was dried to obtain dry pigment G (90 gm, 90%). The pigment has good light fastness.

The tinting shade was 20% stronger than the pigment of example-5.

Example-9

A mixture of 100 gm of crude Pigment G (ball milled with salt sodium sulphate in the ratio 85 part pigment: 15 part sodium sulphate for 24 hours) and 1200 ml dimethyl acetamide was heated to 100° C. and maintained at 100° C. for 2 hours. The mixture was then cooled, filtered and, washed with dimethyl acetamide and water. The obtained product was dried to obtain dry pigment G (89 gm, 89%). The product is suitable for plastic coloration.

Example-10

A mixture of 100 gm of crude Pigment G (ball milled without salt) and 1200 ml dimethyl acetamide was heated to 127° C. and maintained at 127° C. for 2 hours. The mixture was then cooled to 100° C. followed by filtration, washing with dimethyl acetamide and water. The obtained product was dried to obtain dry pigment G (90 gm, 90%). The pigment shows good light fastness. The tinting shade was 10% weaker than the pigment of example-5.

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary. Wherever a range of values is specified, a value up to 10% below and above the lowest and highest numerical value respectively, of the specified range, is included in the scope of the invention.

In view of the wide variety of embodiments to which the principles of the present invention can be applied, it should be understood that the illustrated embodiments are exemplary only. While considerable emphasis has been placed herein on the particular features of this invention, it will be appreciated that various modifications can be made, and that many changes can be made in the preferred embodiments without departing from the principle of the invention. These and other modifications in the nature of the invention or the preferred embodiments will be apparent to those skilled in the art from the disclosure herein, whereby it is to be distinctly understood that the foregoing descriptive matter is to be interpreted merely as illustrative of the invention and not as a limitation.

The invention claimed is:

1. A process for preparing a bis-quinophthalone pigment of Formula (I), said process comprising the following steps;

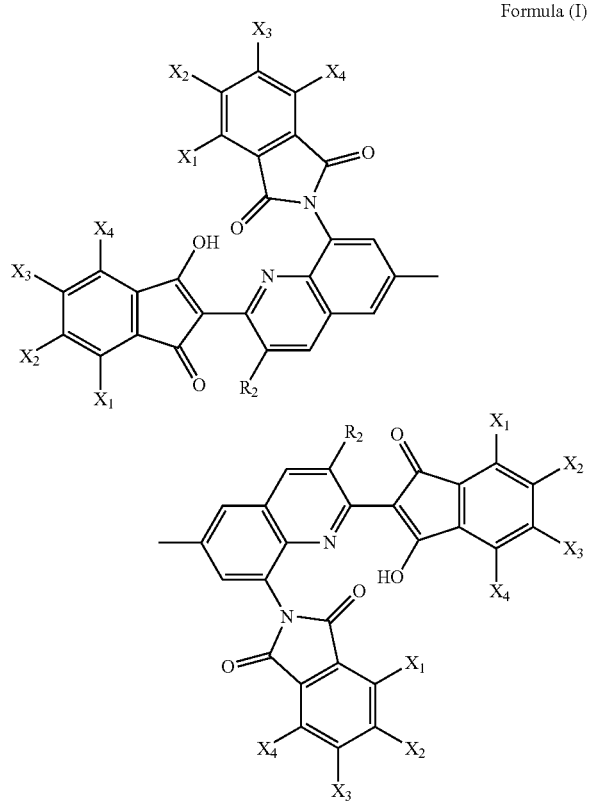

Formula (I)

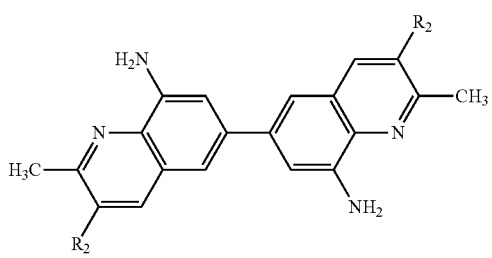

Formula (II)

wherein $X_1$, $X_2$, $X_3$ and $X_4$ are independently H or halogen, preferably Cl or Br;

$R_2$ is substituent selected from the group consisting of H, $C_1$-$C_{20}$ straight or branched chain alkyl substituents, aromatic substituents, aliphatic substituents, and combinations thereof, i. condensing a compound of Formula (II)

wherein $R_2$ is a substituent selected from the group consisting of H, $C_1$-$C_{20}$ straight or branched chain alkyl substituents, aromatic substituents, aliphatic substituents and combinations thereof, with substituted phthalic anhydride of Formula (III)

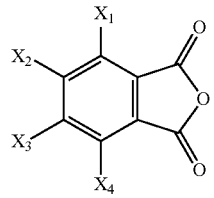

Formula (III)

wherein $X_1$, $X_2$, $X_3$ and $X_4$ are independently H or halogen, preferably Cl or Br, to obtain crude bis-quinophthalone compound of Formula (I); and ii. pigmenting crude bis-quinophthalone compound to obtain a bis-quinophthalone pigment of formula (I).

2. The process as claimed in claim 1, wherein the process step of condensing is carried out in presence of monochlorobenzene and benzoic acid at a temperature in the range of 90° C. to 250° C.

3. The process as claimed in claim 1, wherein the amount of monochlorobenzene is in the range of 1500 ml to 3000 ml per mole of compound of Formula (II).

4. The process as claimed in claim 1, wherein the compound of Formula (II) is 8,8'-diamino-6,6'-bis quinaldine.

5. The process as claimed in claim 1, wherein the amount of benzoic acid is in the range of 3000 gm to 6000 gm per mole of compound of Formula (II).

6. The process as claimed in claim 1, wherein the amount of phthalic anhydride of formula (III) is in the range of 4.0 moles to 6.0 moles per mole of compound of Formula (II).

7. The process as claimed in claim 1, wherein the step of pigmenting is carried in presence of at least one polar solvent selected from the group consisting of dimethyl acetamide, dimethyl formamide, N-methylpyrrolidone and isobutyl alcohol, at a temperature in the range of 80° C. to 150° C.

8. The process as claimed in claim 1, wherein the crude pigment is ball milled for a period of about 20 hours to 36 hours before pigmenting with polar solvent.

9. The process as claimed in claim 1, wherein the crude pigment is ball milled with a salt for a period of about 20 hours to 36 hours before pigmenting with polar solvent.

10. The process as claimed in claim 1, wherein the salt is at least one selected from the group consisting inorganic salts and organic salts.

11. The process as claimed in claim 10, wherein the salt is sodium sulphate.

12. The process as claimed in claim 1, wherein the amount of dimethyl acetamide is in the range of 8 ml to 16 ml per gm of crude pigment.

13. The process as claimed in claim 1, wherein the compound of formula III is tetrachloro phthalic anhydride.

14. A compound of formula I prepared in accordance with the claim 1, wherein, $R_2$ is H and $X_1$, $X_2$, $X_3$ and $X_4$ are Cl.

* * * * *